United States Patent
Holdaway et al.

(10) Patent No.: US 12,274,479 B2
(45) Date of Patent: Apr. 15, 2025

(54) CEMENT DELIVERY GUIDES AND CORRESPONDING FENESTRATED SCREWS

(71) Applicant: Warsaw Orthopedic, Inc., Warsaw, IN (US)

(72) Inventors: Anela Camdzic Holdaway, Cordova, TN (US); Brian A. Butler, Millington, TN (US); William Alan Rezach, Covington, TN (US); Mark R. Grizzard, Munford, TN (US); Julien J. Prevost, Memphis, TN (US); Aubrey R. Mills, Memphis, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 353 days.

(21) Appl. No.: 17/860,303

(22) Filed: Jul. 8, 2022

(65) Prior Publication Data
US 2024/0008909 A1  Jan. 11, 2024

(51) Int. Cl.
*A61B 17/88* (2006.01)
*A61B 17/70* (2006.01)
*A61B 17/86* (2006.01)

(52) U.S. Cl.
CPC ...... *A61B 17/8816* (2013.01); *A61B 17/7032* (2013.01); *A61B 17/7076* (2013.01); *A61B 17/7098* (2013.01); *A61B 17/864* (2013.01); *A61B 17/8805* (2013.01); *A61B 17/8811* (2013.01); *A61B 17/8819* (2013.01)

(58) Field of Classification Search
CPC .............. A61B 17/7098; A61B 17/864; A61B 17/8805; A61B 17/8811; A61B 17/8816; A61B 17/8819
See application file for complete search history.

(56) References Cited

U.S. PATENT DOCUMENTS

| | | | |
|---|---|---|---|
| 8,747,411 B2 | 6/2014 | Mitchell | |
| 9,326,801 B2 | 5/2016 | Poulos | |
| 9,814,506 B2 | 11/2017 | Donahue | |
| 9,993,276 B2 * | 6/2018 | Russell | A61B 17/8695 |
| 10,052,140 B2 | 8/2018 | Krause et al. | |
| 10,105,165 B2 * | 10/2018 | Biedermann | A61B 17/7001 |
| 10,888,363 B2 | 1/2021 | Greenhalgh et al. | |
| 11,026,736 B2 | 6/2021 | Rohlfing et al. | |

(Continued)

OTHER PUBLICATIONS

International Search Report and Written Opinion in Application No. PCT/IB2023/056847 dated Nov. 8, 2023.

*Primary Examiner* — Larry E Waggle, Jr.
(74) *Attorney, Agent, or Firm* — FOX ROTHSCHILD LLP

(57) ABSTRACT

Various bone cement guides are disclosed that may connect directly to a fenestrated bone screw or connect to a spinal construct that is coupled to a fenestrated bone screw. In various embodiments, cement guides may include a three-part assembly including a hollow outer sleeve and a hollow inner sleeve with a removable inner rod. In various embodiments, the hollow inner sleeve may be movable between a retracted position and an extended position and in the extended position a distal end of the inner sleeve may splay outward and capture the head portion of a fenestrated bone screw. In other embodiments, a distal end of the outer sleeve may surround and capture tabs of an extended tulip head connector while the inner sleeve couples to an inside surface of the extended tulip head connector.

19 Claims, 20 Drawing Sheets

(56) References Cited

U.S. PATENT DOCUMENTS

| | | |
|---|---|---|
| 11,083,501 B2 | 8/2021 | Grizzard et al. |
| RE48,870 E | 1/2022 | Jones et al. |
| 2009/0264895 A1 | 10/2009 | Gasperut et al. |
| 2012/0203287 A1 | 8/2012 | Arambula et al. |
| 2013/0103094 A1 | 4/2013 | Beale et al. |
| 2015/0257797 A1 | 9/2015 | Biedermann et al. |
| 2016/0235450 A1 | 8/2016 | Walker et al. |
| 2020/0275961 A1 | 9/2020 | May |
| 2020/0390484 A1 | 12/2020 | Emil et al. |
| 2021/0290282 A1 | 9/2021 | Rohlfing et al. |
| 2021/0307792 A1 | 10/2021 | Grizzard et al. |
| 2022/0192711 A1* | 6/2022 | Biedermann ........ A61B 17/864 |

* cited by examiner

CEMENT DELIVERY GUIDES AND CORRESPONDING FENESTRATED SCREWS

CROSS REFERENCE TO RELATED APPLICATIONS

This application incorporates by reference the entire disclosure of U.S. Pat. No. 11,083,501 titled Surgical System and Method filed on Apr. 24, 2019 and U.S. application Ser. No. 17/354,450 titled Surgical System and Method filed on Jun. 22, 2021. This application also incorporates by reference the entire disclosure of U.S. Pat. No. 11,026,736 titled Surgical Instrument and Method filed on Feb. 19, 2018 and U.S. application Ser. No. 17/338,909 titled Surgical Instrument and Method filed on Jun. 4, 2021. This application also incorporates by reference the entire disclosure of US Pat. Pub. No 20090264895 titled Systems and methods for implanting a bone fastener and delivering a bone filling material filed on Apr. 22, 2008. The entire disclosure of each of the above references is hereby incorporated by reference in its entirety.

FIELD

The present technology is generally related to surgical tools and fenestrated bone screws for the delivery of cement or other flowable materials to boney anatomy of a patient, e.g., the posterior thoracolumbar and/or sacral space of the spine.

BACKGROUND

In select surgeries a bone screw may be installed in a patient and flowable materials such as bone growth promoting material (BGM) and/or cement may be used to further strengthen or solidify the bone screw to the boney anatomy or promote fusion. In some applications, a fenestrated bone screw having a through hole therein may be used to channel delivery of BGM and/or cement through and around the bone screw. Various tools may be used to deliver the BGM and/or cement material to the target location.

SUMMARY

The techniques of this disclosure generally relate to tools and fenestrated bone screws for delivering BGM and/or cement to a target location.

In one aspect, the present disclosure provides for a surgical tool, such as a bone cement guide or guide for the delivery of other flowable materials, for delivering bone cement or other flowable materials. Throughout this disclosure reference has been made to a "bone cement guide," but it should be appreciated that this guide may be provided for other flowable materials, such as BGM. In various embodiments, a bone cement guide may include a hollow outer sleeve having an elongated cylindrical shape and a hollow inner sleeve having an elongated cylindrical shape. In various embodiments, the hollow inner sleeve may be disposed inside of the hollow outer sleeve and have a first thread pattern at a proximal end thereof and a coupling portion at a distal end thereof, for example. In various embodiments, the hollow inner sleeve may be movable between a retracted position and an extended position, for example. In various embodiments, a hollow inner rod may be removably disposable within the hollow inner sleeve and have a distal end that is configured to guide bone cement to a bone screw, for example. In various embodiments, the hollow inner rod may include a second thread pattern having a size and shape corresponding to a size and shape of the first thread pattern, for example. In some embodiments, in the extended position, the coupling portion extends beyond a distal end of the hollow outer sleeve and is configured to splay outward to surround and capture a head portion of the bone screw, for example. In some embodiments, in the retracted position, the coupling portion is moved inside of a distal end of the hollow outer sleeve and constrained from splaying outward thereby securely coupling the surgical tool to the head portion of the bone screw, for example. In another aspect, the disclosure provides for a surgical system for delivering bone cement to a target site, for example a bone cement guide. In various embodiments, the system may include a surgical implant including U-shaped connector having a first connection tab and a second connection tab opposite the first connection tab, the U-shaped connector may be configured to couple to a head portion of a bone screw in a lower cavity, for example. In various embodiments, the guide may include a hollow outer sleeve having an elongated cylindrical shape and a distal end comprising a first engagement tab and a second engagement tab opposite the first engagement tab, for example. In at least some embodiments, the first engagement tab may be configured to couple to the first connection tab and the second engagement tab may be configured to couple to the second connection tab, for example. In various embodiments, a hollow inner sleeve may have an elongated cylindrical shape and a distal end comprising a third engagement tab and a fourth engagement tab opposite the third engagement tab, may be provided for. In various embodiments, the hollow inner sleeve may be disposed inside of the hollow outer sleeve and have a first thread pattern at a proximal end thereof, and the hollow inner sleeve may be movable between a retracted position and an extended position, for example. In various embodiments, a bone cement guide may include a hollow inner rod removably disposable within the hollow inner sleeve and having a distal end configured to guide bone cement to the head portion of the bone screw while it is disposed in the lower cavity of the U-shaped connector, for example. In at least some embodiments, the hollow inner rod may include a second thread pattern having a size and shape corresponding to a size and shape of the first thread pattern, for example. In at least some embodiments, in the extended position the third engagement tab and the fourth engagement tab each extend beyond the distal end of the hollow outer sleeve, and in the retracted position the first engagement tab and the second engagement tab extend beyond a distal end of the hollow inner sleeve, for example.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
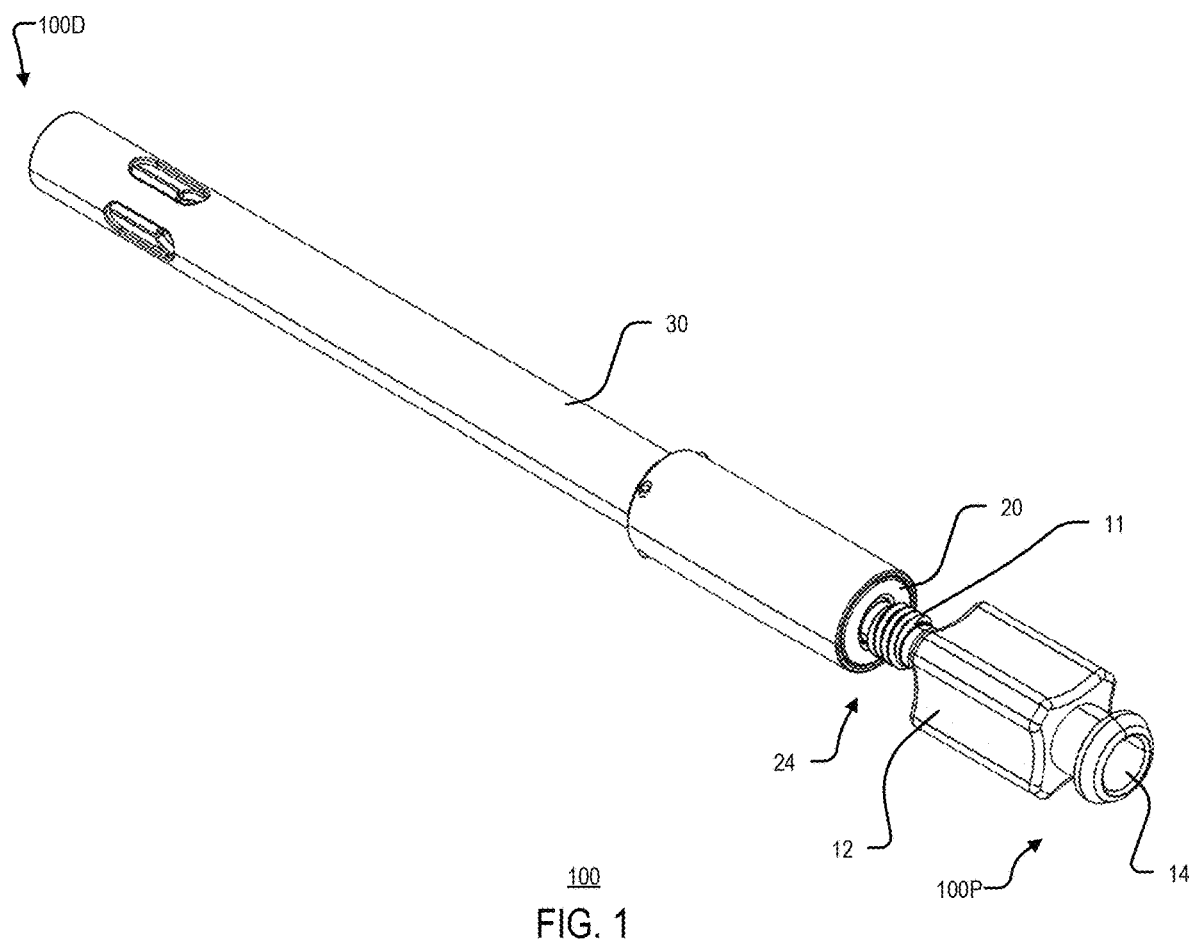
FIG. 1 is a first perspective view of a first embodiment of a cement delivery guide.

Embodiments of the present disclosure relate generally, for example, to spinal stabilization systems, and more particularly, to surgical instruments for use with spinal stabilization systems. Embodiments of the devices and methods are described below with reference to the Figures.

The following discussion omits or only briefly describes certain components, features and functionality related to medical implants, installation tools, and associated surgical techniques, which are apparent to those of ordinary skill in the art. It is noted that various embodiments are described in detail with reference to the drawings, in which like reference numerals represent like parts and assemblies throughout the several views, where possible. Reference to various embodiments does not limit the scope of the claims appended hereto because the embodiments are examples of the inventive concepts described herein. Additionally, any example(s) set forth in this specification are intended to be non-limiting and set forth some of the many possible embodiments applicable to the appended claims. Further, particular features described herein can be used in combination with other described features in each of the various possible combinations and permutations unless the context or other statements clearly indicate otherwise.

Terms such as "same," "equal," "planar," "coplanar," "parallel," "perpendicular," etc. as used herein are intended to encompass a meaning of exactly the same while also including variations that may occur, for example, due to manufacturing processes. The term "substantially" may be used herein to emphasize this meaning, particularly when the described embodiment has the same or nearly the same functionality or characteristic, unless the context or other statements clearly indicate otherwise.

Referring to FIGS. 1-20 generally, various delivery systems 100, 200 are disclosed for delivering cement or other flowable materials. The components of disclosed systems can be fabricated from biologically acceptable materials suitable for medical applications, including metals, synthetic polymers, ceramics, and bone material and/or their composites. For example, the components, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe, polylactic acid or polylactide and their combinations. As used herein, the term "bone cement" may be used to refer to any known filling composition which may be used as an adhesive and/or as a bone growth promoting material. In some embodiments, bone cement may be a flowable material with any suitable viscosity which may be used alone or in combination with a non flowable material, such as a bone graft, for example. In various embodiments, "bone cement" may refer to a material having an osteoinductive demineralized bone matrix (DBM) such as a material sold by Medtronic of Minneapolis Minnesota under the trade name "Grafton." Another example material may be Hydroxyapatite, a polymethylmethacrylate (PMMA) bone cement containing hydroxyapatite; and the Kyphon HV-R Bone Cement and its variation formulas sold by Medtronic of Minneapolis Minnesota under the trade name "Kyphon." An example bone graft material may include a recombinant human bone morphogenetic protein-2 (rhBMP-2), such as a material sold by Medtronic of Minneapolis Minnesota under the trade name "Infuse" and/or "Magnifuse." In some embodiments, bone cement may be formed shortly before injection at a target site by a two-part system in which an epoxy like substance is mixed with a bone growth promoting material in a mixing device and shortly after mixing the material begins to cure from a low viscosity, relatively free flowing liquid, to a hardened less flowable state.

Figure 2:
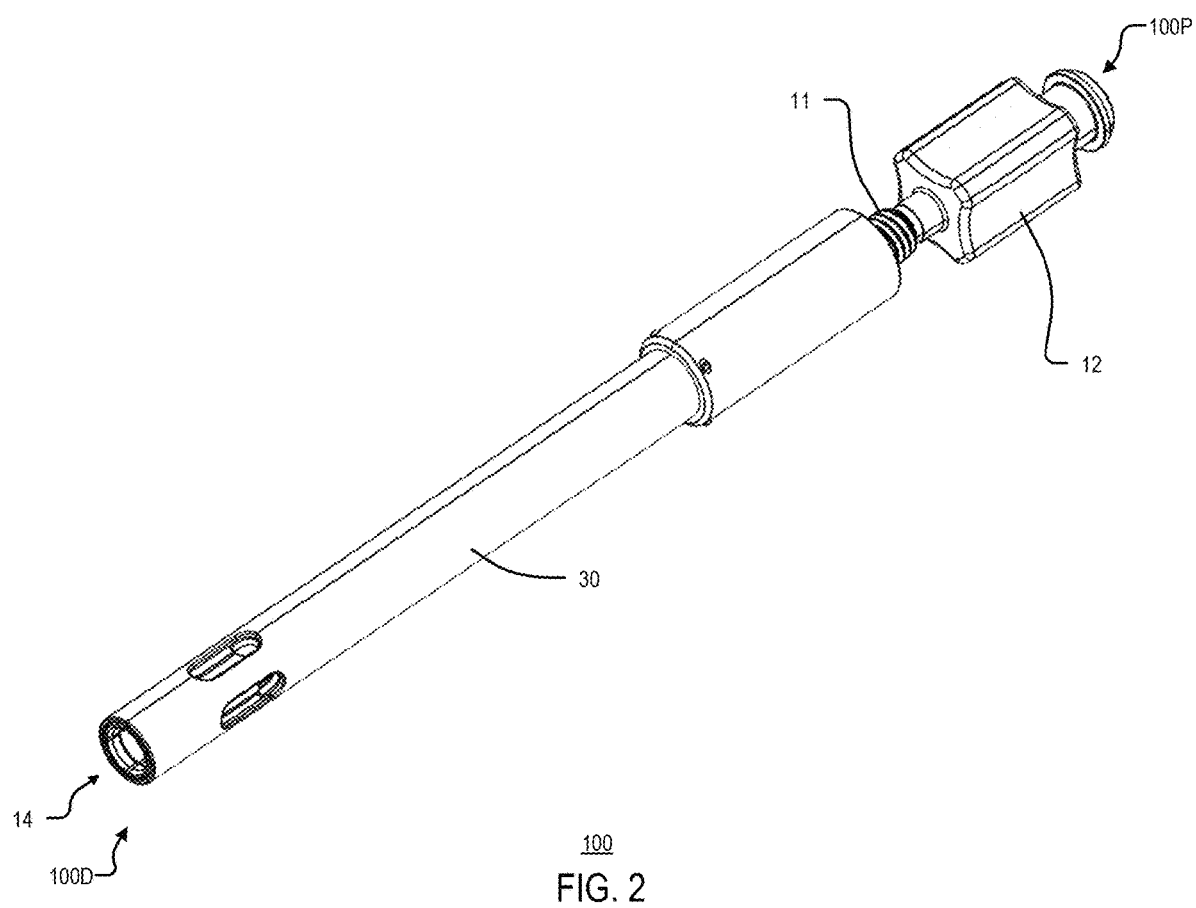
FIG. 2 is a second perspective view of a cement delivery guide.
Figure 3:
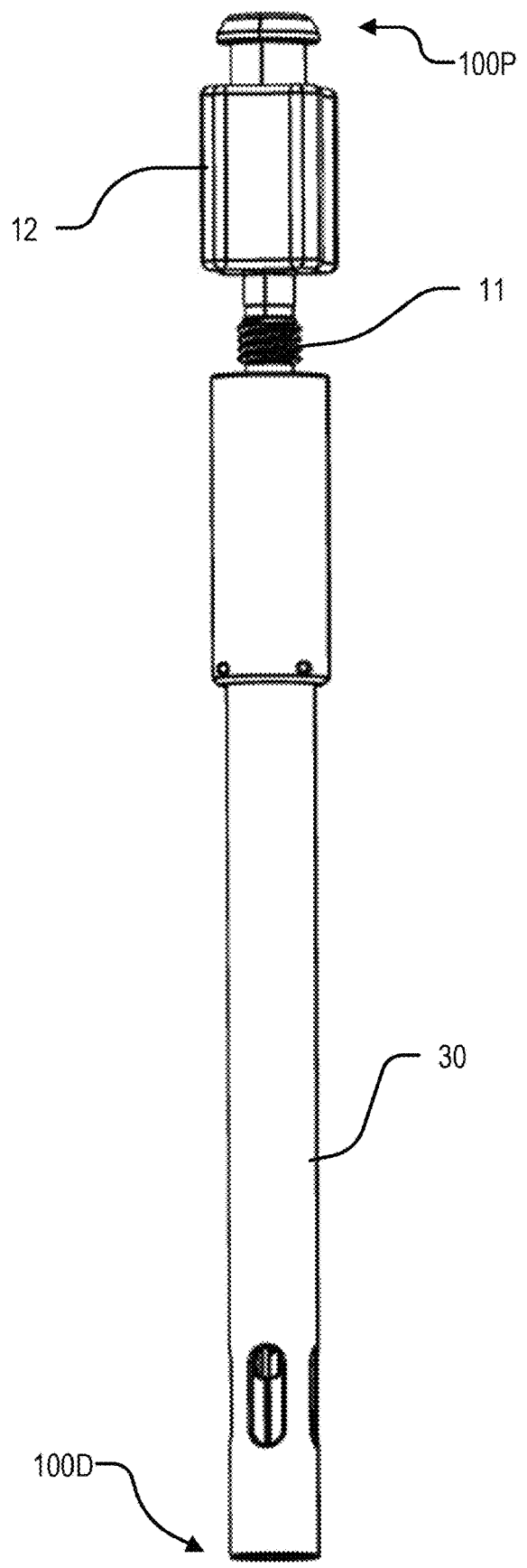
FIG. 3 is a front view of a cement delivery guide.
Figure 4:
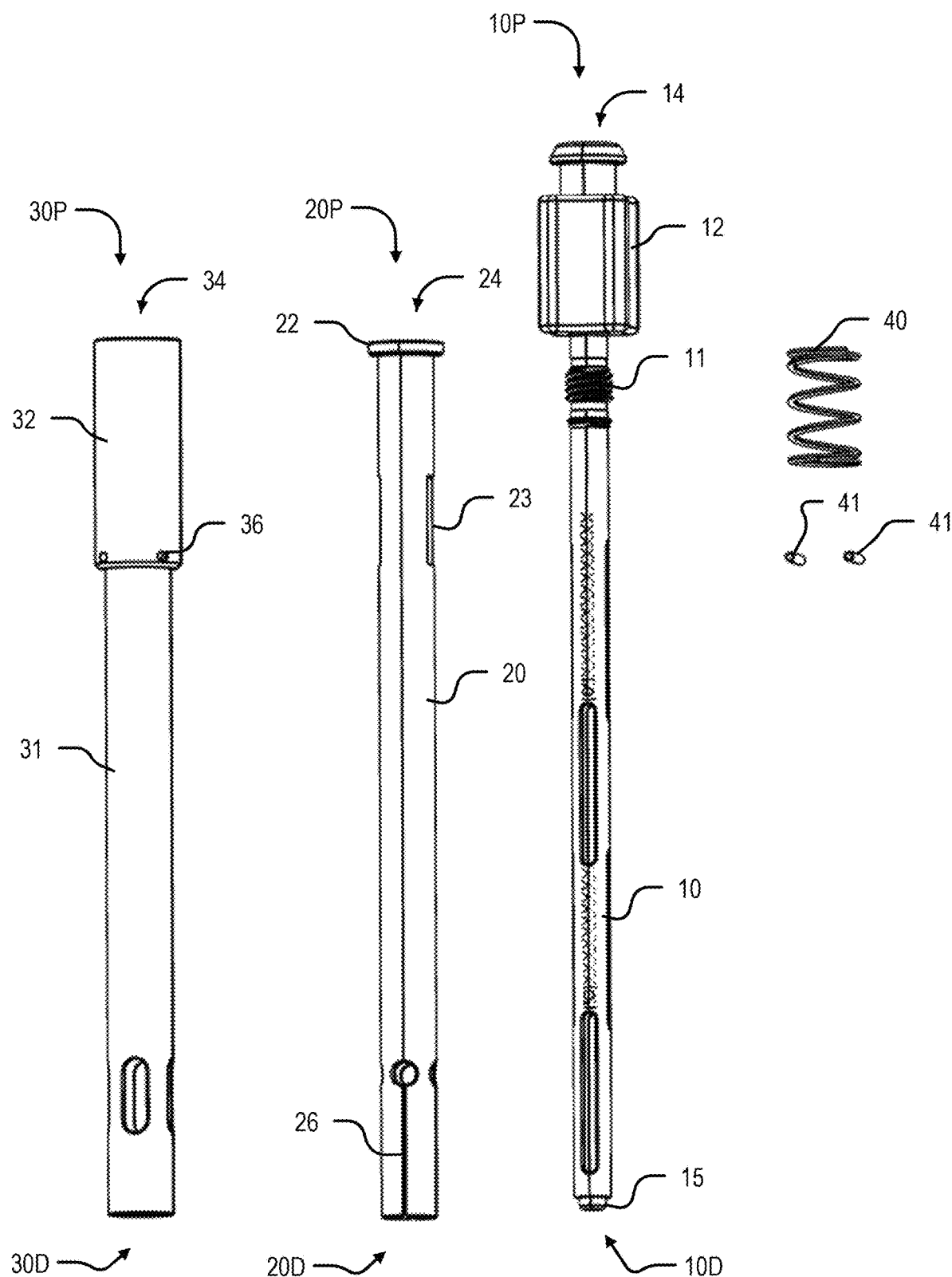
FIG. 4 is a first exploded parts view of a cement delivery guide.
Figure 5:
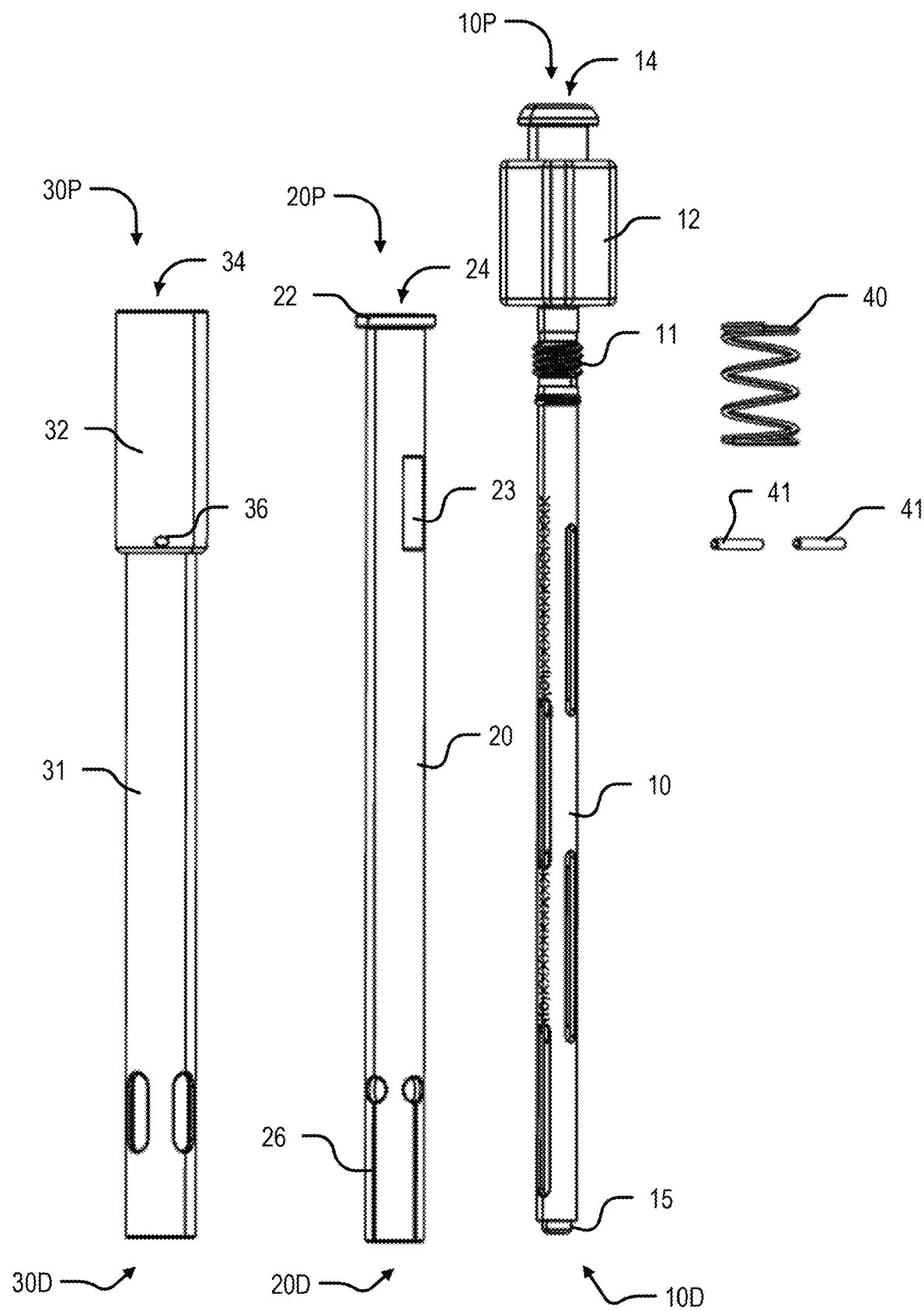
FIG. 5 is a second exploded parts view of a cement delivery guide.
Figure 6:
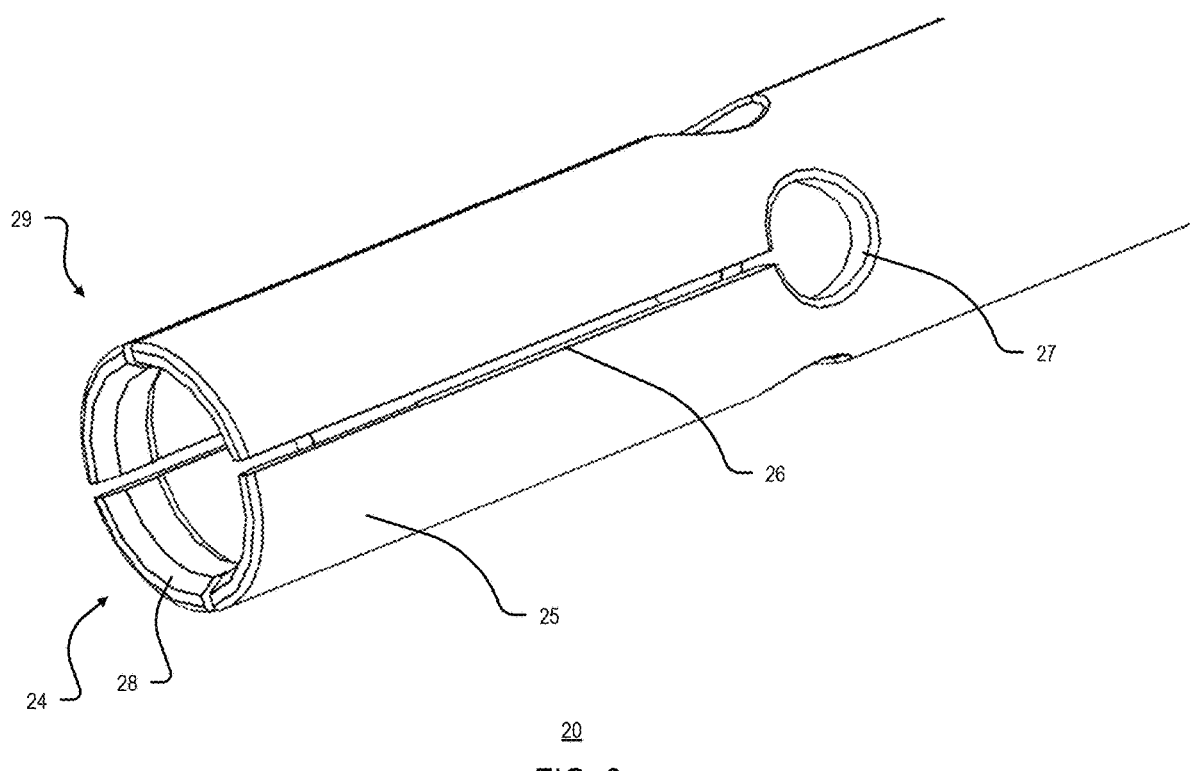
FIG. 6 is an enlarged view of a distal end of an inner sleeve of a cement delivery guide.
Figure 7:
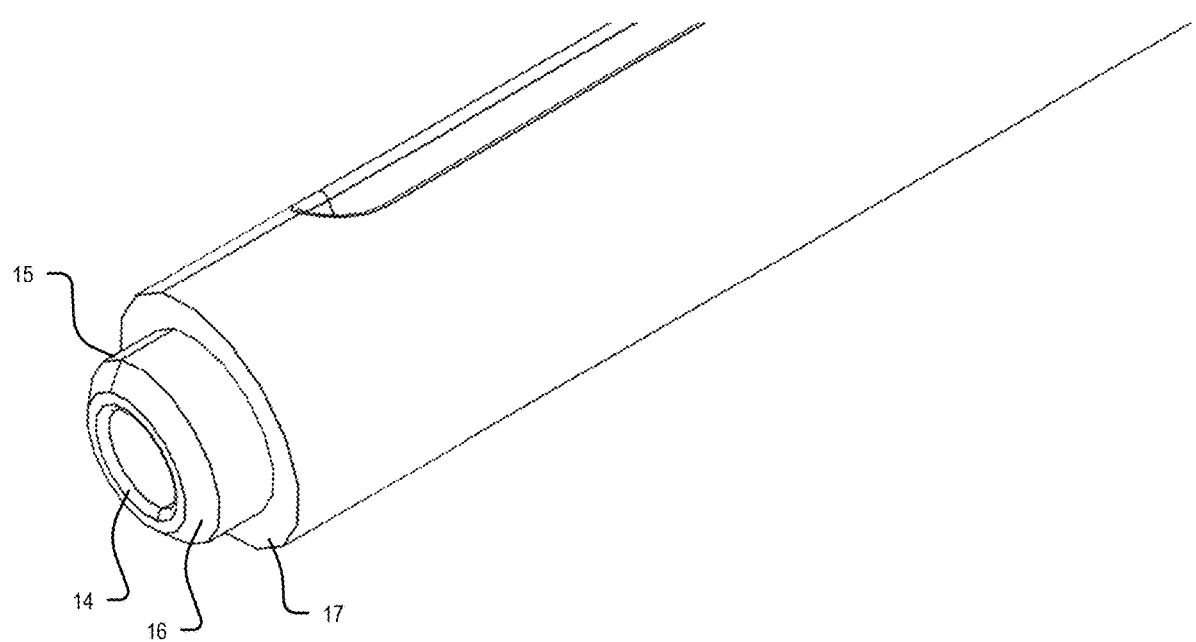
FIG. 7 is an enlarged view of a distal end of an inner rod of a cement delivery guide.

Referring generally to FIGS. 1-11 a first embodiment of a delivery system is disclosed for various flowable materials including, for example, cements. FIGS. 1-3 are various perspective views of a cement delivery guide 100. FIGS. 4-5 are various exploded parts views of a cement delivery guide 100. FIG. 6 is an enlarged view of a distal end of an inner sleeve 20 of a cement delivery guide 100 and FIG. 7 is an enlarged view of a distal end of an inner rod 10 of a cement delivery guide 100.

In the example embodiment, a cement delivery guide 100 extends in a longitudinal direction from a proximal end 100P to a distal end 100D. As seen best in the exploded parts views of FIGS. 4-5, the guide 100 may include a three-part assembly including a hollow outer sleeve 30, a hollow inner sleeve 20, and a hollow inner rod 10. In various embodiments, the outer sleeve 30 extends in a longitudinal direction from a proximal end 30P to a distal end 30D and includes a central aperture 34 extending from the proximal end 30P to the distal end 30D. Additionally, the outer sleeve 30 may include a first portion 32 and a second portion 31 in which the first portion 32 defines a portion of the aperture 34 having a relatively larger interior diameter than the interior diameter of the second portion 31.

In the example embodiment, the hollow inner sleeve 20 may extend in a longitudinal direction from a proximal end 20P to a distal end 20D and include a central aperture 24 extending from the proximal end 20P to the distal end 20D. In various embodiments, the inner sleeve 20 may be disposed inside of aperture 34 and be movably coupled with the outer sleeve 30 such that the inner sleeve 20 may move forward and backward in the longitudinal direction across a distance generally corresponding to a length of the first portion 32 in the longitudinal direction. In some embodiments, the inner sleeve 20 may move forward and backward in the longitudinal direction across a distance that is less than the full length of the first portion 32 in the longitudinal direction. In the example embodiment, the inner sleeve 20 may include a necked down portion 23 which may be necked down to accommodate positioning pins 41 extending through pin holes 36. In some embodiments, pins 41 may not be included. Additionally, a biasing element, such as a coil spring 40, may be disposed inside of the first portion 32 to bias the inner sleeve 20 towards a retracted position. For example, spring 40 may apply a force that urges stop ring 22 of inner sleeve 20 in a proximal direction, i.e., towards proximal end 30P of outer sleeve. In this way, inner sleeve 20 may be movably coupled to outer sleeve 30 such that it may move forward and backward in the longitudinal direction between a neutral position (i.e., the retracted position) and an extended position. In other embodiments, a spring 40 may not be included. As will be explained in more detail below, in the extended position the distal end 20D of the inner sleeve 20 may extend farther than the distal end 30D of outer sleeve 30, e.g., farther in a distal direction.

In the example embodiment, inner rod 10 may extend in a longitudinal direction from a proximal end 10P to a distal end 10D and include a central aperture 14 extending from the proximal end 10P to the distal end 10D. In various embodiments, the inner rod 10 may be removably disposed and/or coupled with inner sleeve 20. For example, inner rod 10 may be disposed inside of aperture 24. Additionally, inner rod 10 may include a threaded portion 11 that may thread to a corresponding threaded portion at the proximal end of aperture 24 (see FIG. 1). In this way, the inner rod 10 may be threadably engaged with corresponding threads of aperture 24 having a corresponding size and shape to the thread pattern of threaded portion 11. Accordingly, an end user may couple and uncouple inner rod 10 to inner sleeve 20 by rotating handle 12 thereby engaging the threaded portion 11 of inner rod 10 with the threaded portion of aperture 24. As will be explained in further detail below, the distal end 10D of inner rod may include an engagement feature 15 having a size and shape corresponding to a drive feature 52 and/or counterbore 56 opening of a fenestrated bone screw 50 (see FIGS. 8-9). In some embodiments, engagement feature 15 may be referred to as a distal most tip or orifice.

As seen best in FIG. 6, a distal end 20D of inner sleeve 20 may include a coupling portion 29 surrounding a distal end 20D of aperture 24. In the example embodiment, coupling portion 29 may be configured to couple to a head portion 51 of a bone screw 50 by capturing the head portion 51 of the bone screw 50 between tangs 25, for example. In various embodiments, inner sleeve 20 may include at least one deformable tang 25 that is configured to splay outward from a central axis of aperture 24, e.g., to splay outward in an opposing direction away from the longitudinal extension direction defined by aperture 24. In the example embodiment, coupling portion 29 includes four deformable tangs 25 that are equally spaced around a circumference of a distal end 20D of aperture 24. Each tang 25 may be delineated by an adjacent pair of slits 26 that form gaps in the distal end 20D and extend in the longitudinal direction from the distal end 20D towards the proximal end 20P for a relatively short distance. In the example embodiment, each slit 26 extends from a distal most end 20D towards a relief aperture 27. This configuration may allow for an elastic deformation in which tangs 25 splay outward momentarily to surround and capture the head portion 51 of a bone screw 50. Additionally, an interior circumference of the distal most end 20D of aperture 24 may include a circumferential rim or lip portion 28 that facilitates retaining the head portion 51 of bone screw 50. For example, an interior surface of tangs 25 may include a lip portion 28 and/or arcuate rim. In use, a surgeon may extend inner sleeve 20 from the retracted position to an extended position where coupling portion 29 is exposed. Thereafter, the surgeon may push down on sleeve 20 such that coupling portion 29 is in direct contact with head portion 51 of bone screw 50 and by doing so the tangs 25 of coupling portion 29 may splay outward to accommodate the relative wide medial portion of the head 51 of bone screw 50 and then retract back to a non-deformed state to retain the head portion 51 of bone screw 50 via the underside of the head portion 51. For example, the circumferential lip 28 may directly contact the underside of head portion 51 once it is captured by tangs 25. Additionally, the spring 40 may urge the inner sleeve 20 back towards the retracted position causing the coupling portion 29 to retract inside of the aperture 34 of outer sleeve 30 and the inside surfaces of aperture 34 may prevent the tangs 25 from splaying outward thereby securely retaining the bone screw 50 by the cooperation of outer sleeve 30 and inner sleeve 20.

As seen best in FIG. 7, a distal end 10D of inner rod 10 may include an engagement feature 15. In various embodiments, engagement feature 15 may have a size and shape corresponding to a drive feature 52 of a bone screw 50. Accordingly, engagement feature 15 may take any suitable shape corresponding to the particular drive feature 52 of bone screw. In various embodiments, engagement feature 15 may have a substantially circular shape as illustrated, or alternatively engagement feature 15 may generally correspond to a torx, polygonal, square, or hexolobular shape. In the example embodiment, engagement feature 15 comprises an annular ring like shape having an inclined portion 16 that generally surrounds a distal most end of aperture 14. In other embodiments, portion 16 may have a relatively flat surface, a planar surface, or be inclined to an even greater extent than illustrated. In at least one embodiment, an end user may insert engagement feature 15 into drive feature 52 of bone screw 50 while stop surface 17 directly contacts an uppermost surface of head portion 51 of bone screw 50 (see FIG. 11). In some embodiments, stop surface 17 may be substantially flat or planar.

Figure 8:
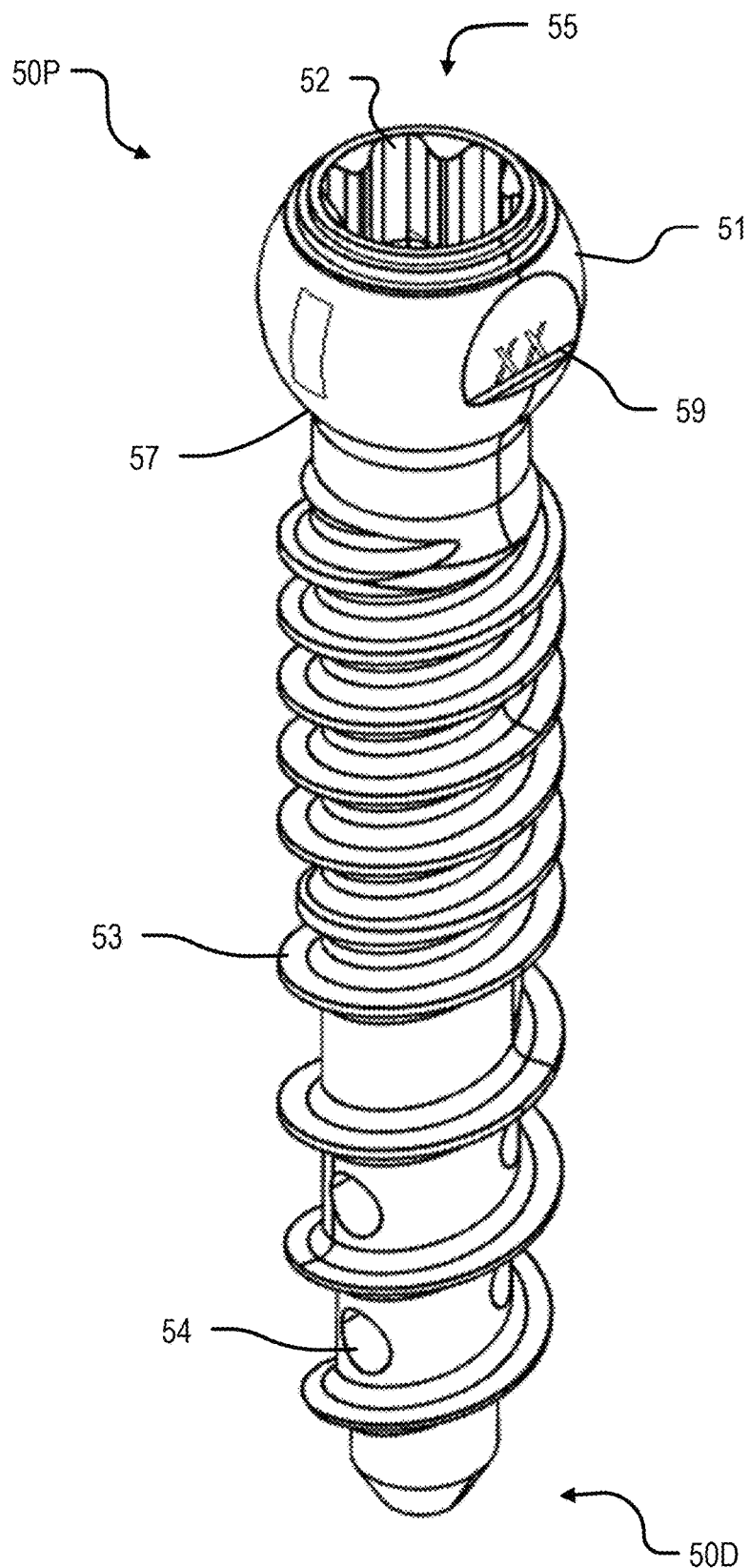
FIG. 8 is a perspective view of a fenestrated bone screw.
Figure 9:
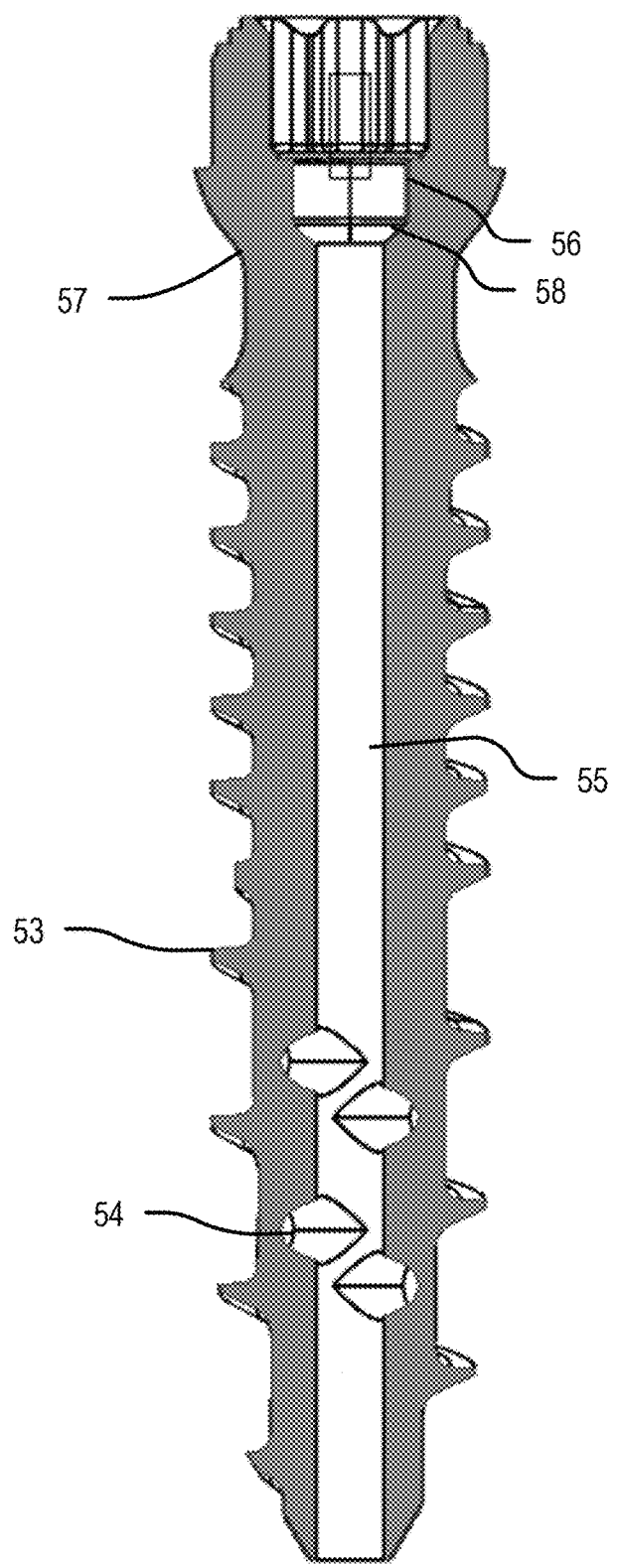
FIG. 9 is a cross section view of a fenestrated bone screw.

FIGS. 8-9 illustrate an example fenestrated bone screw 50. FIG. 8 is a perspective view of a fenestrated bone screw 50, and FIG. 9 is a cross section view of a fenestrated bone screw 50. In the example embodiment, bone screw 50 may include any suitable type of threads 53 and a monoaxial or polyaxial head 51. As illustrated, bone screw 50 may include a head portion 51 having a generally spherical shape with a drive feature 52 at an upper end thereof and an underside 57 (lower end of head 51). In various embodiments, head 51 may include a planar side surface 59 that allows for coupling of a spinal implant, such as a tulip bulb connector, to bone screw 50. In the example embodiment, bone screw 50 is a fenestrated bone screw including an aperture 55 or channel extending through bone screw 50 from a proximal end 50P to a distal end 50D (see FIG. 9). Channel 55 may allow for bone cement to be injected therein such that the bone cement flows through channel 55 at a proximal end 50P towards and out of the distal end 50D. Additionally, in some embodiments channel 55 may provide a flow path for bone cement through fenestrations 54, which may be a second form of aperture extending through a sidewall of bone screw 50 that communicates with channel 55, for example. In the example embodiment, bone screw 50 may include a counterbore 56 having an angled portion 58 that facilitates the movement of bone cement through channel 55. For example, counterbore 56 may facilitate funneling of bone cement through channel 55.

Figure 10:
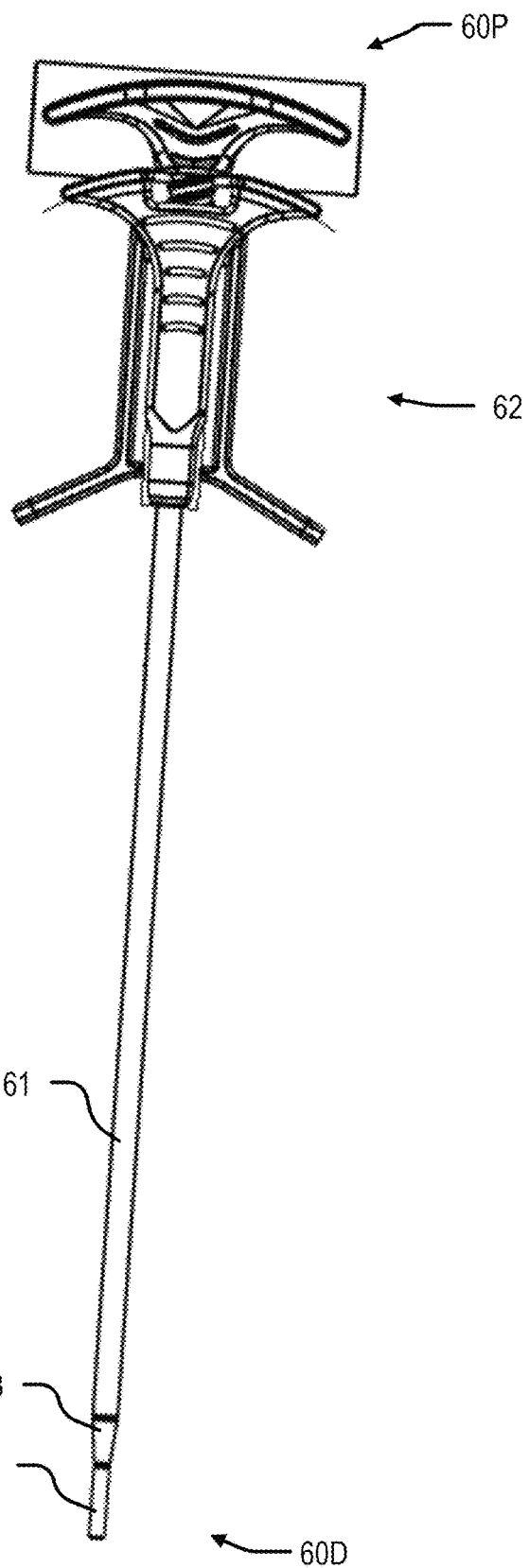
FIG. 10 is a perspective view of a cement delivery device.

FIG. 10 is a perspective view of a cement delivery device (CDD 60). In some embodiments, cement delivery device 60 may be referred to as a cement delivery tube. In the example embodiment, CDD 60 may include a hollow shaft 61 that extends in a longitudinal direction from a proximal end 60P to a distal end 60D. In the example embodiment, an outer diameter of shaft 61 may correspond in size and shape to an inner diameter of inner rod 10, for example. Additionally, hollow shaft 61 may include a necked down portion 63 and a minor diameter tip portion 64 adjacent a distal end 60D. CDD 60 may include any suitable handle assembly 62 which may be depressed and or squeezed by an end user to push bone cement through an interior of shaft 61 and out of distal end 60D.

Figure 11:
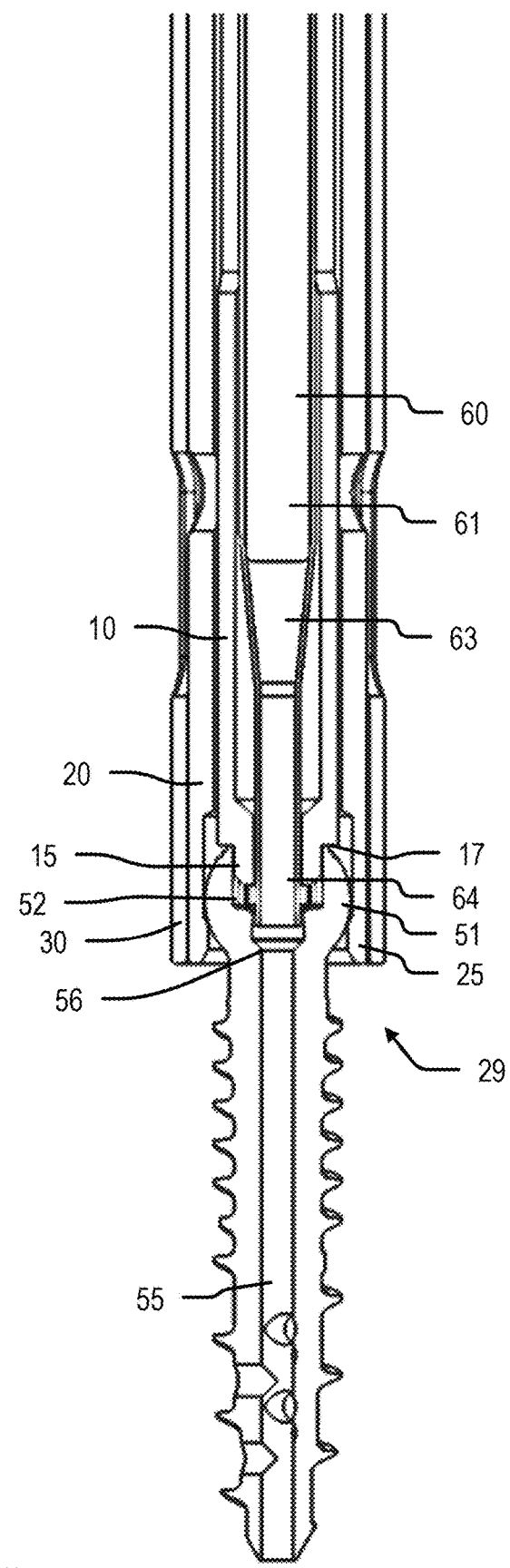
FIG. 11 is a cross section view of a cement delivery guide coupled to a fenestrated bone screw and a cement delivery device inserted into a counterbore of the fenestrated bone screw.
Figure 12:
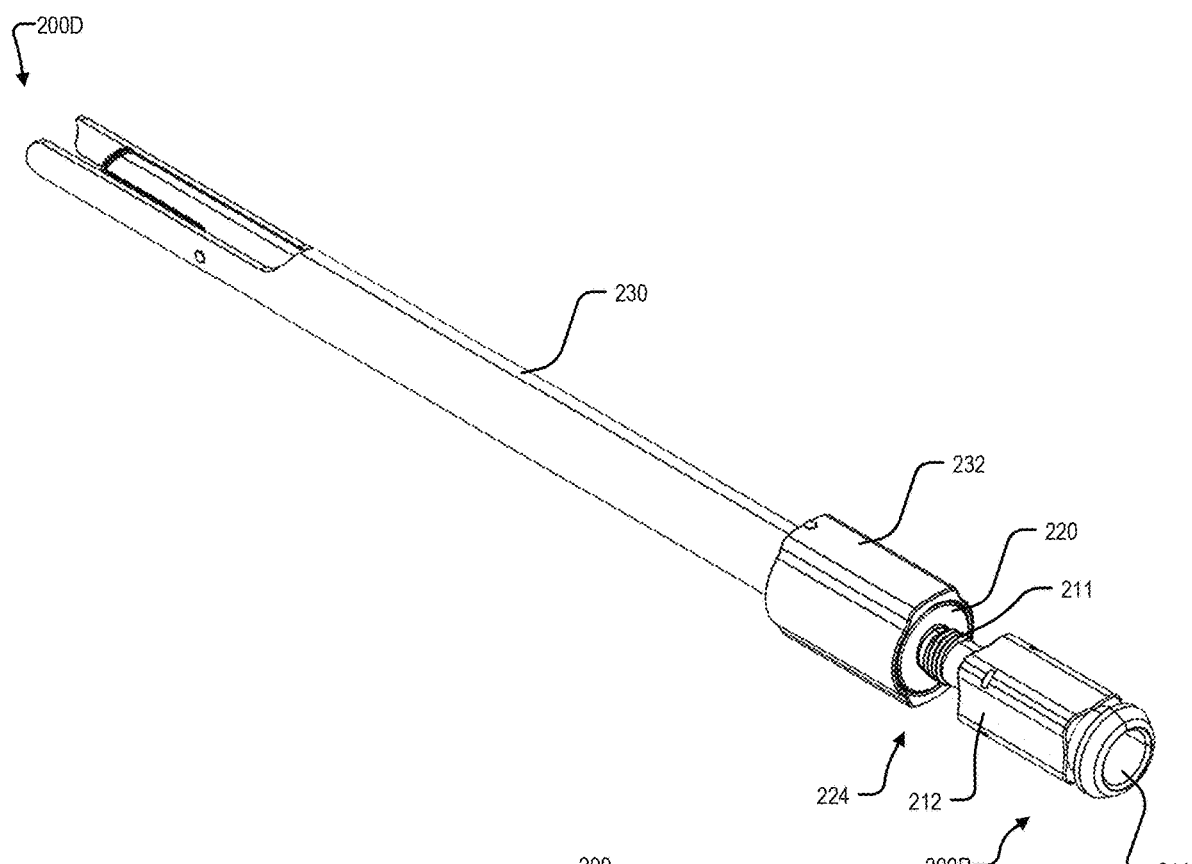
FIG. 12 is a first perspective view of a second embodiment of a cement delivery guide.
Figure 13:
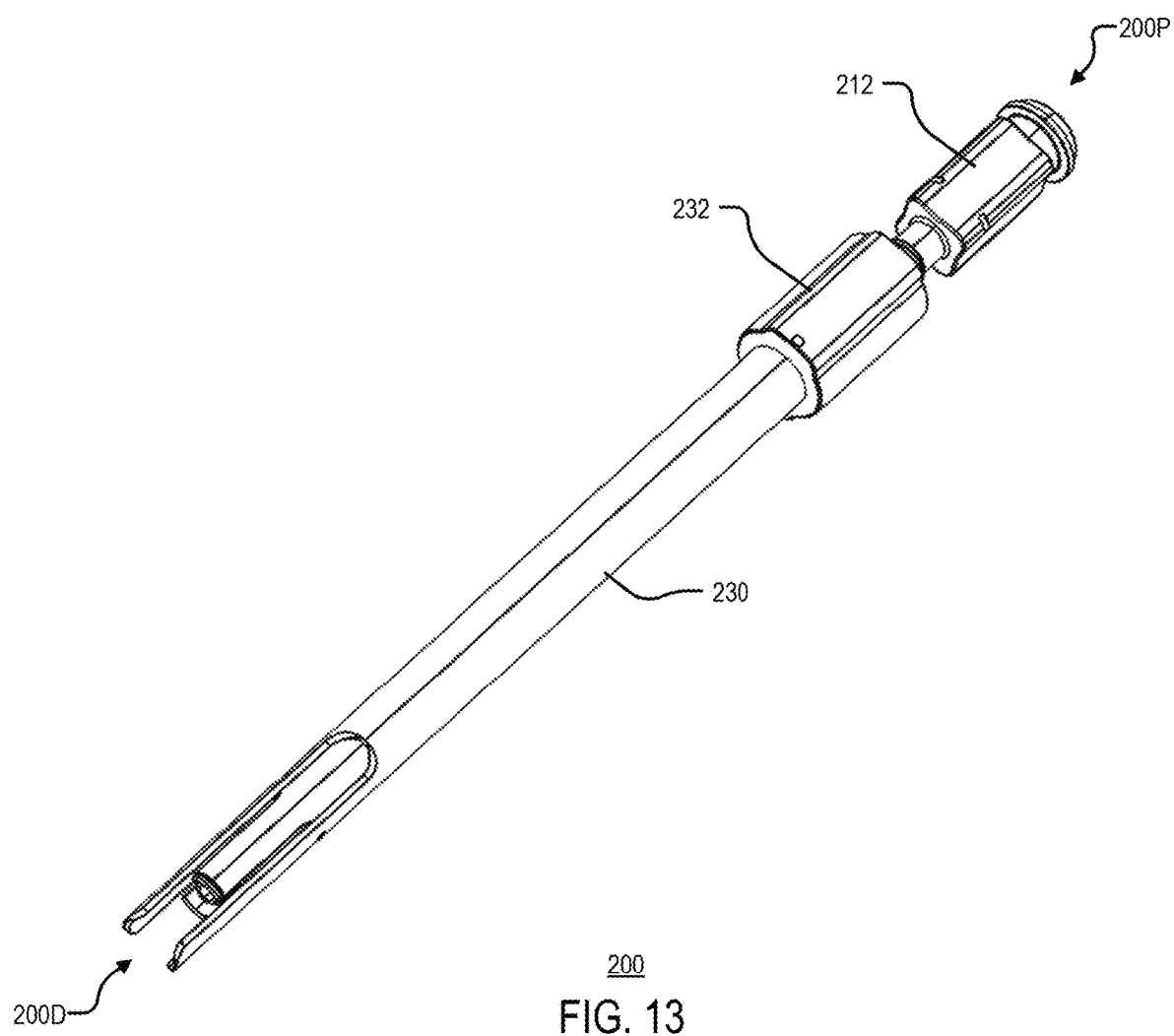
FIG. 13 is a second perspective view of a cement delivery guide.
Figure 14:
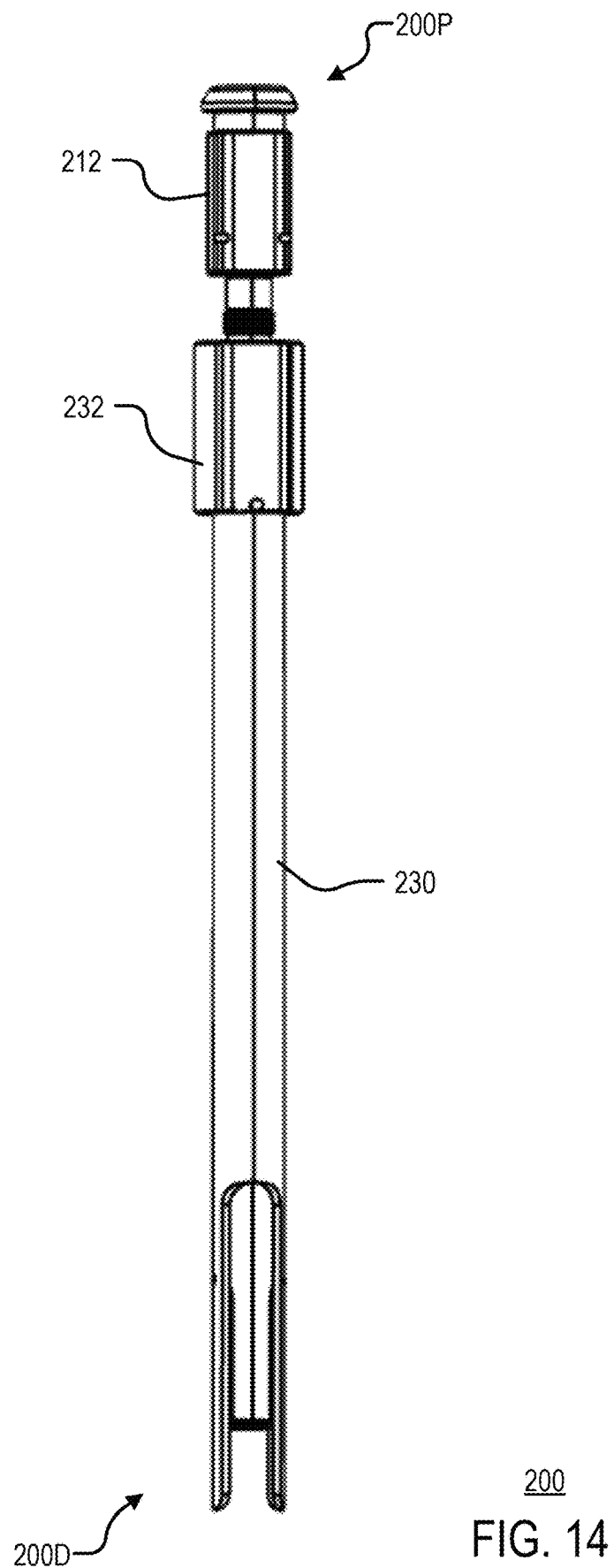
FIG. 14 is a front view of a cement delivery guide.

FIG. 11 is a cross section view of bone cement guide 100 and CDD 60 in operation. As illustrated, coupling portion 29 of inner sleeve 20 is securely coupled to head portion 51 of bone screw 50. For example, tangs 25 surround and capture head portion 51 of bone screw 50 and are prevented from splaying outward by outer sleeve 30 due to inner sleeve 20 being positioned in the retracted position. Additionally, inner rod 10 is threadably engaged with inner sleeve 20 such that engagement feature 15 is partially inserted within drive feature 52 of bone screw 50 while stop surface 17 directly contacts an uppermost surface of head portion 51. Furthermore, CDD 60 may be insert inside of inner rod 10 such that shaft 61 extends therethrough and a tip portion 64 is fully seated inside of counterbore 56. In this way, CDD 60 may deliver bone cement through cement delivery guide 100 directly into the counterbore portion 56 of fenestrated bone screw 50. In the example embodiment, engagement feature 15 may not fully extend into the counterbore portion 56 although in some embodiments it may. For example, in some embodiments, engagement feature 15 (or a portion thereof) may have a size and shape generally corresponding to a size and shape of counterbore 15 such that no CDD is required to deliver bone cement to fenestrated bone screw 50.

Referring generally to FIGS. 12-20 a second embodiment of a bone cement delivery system is disclosed. The second embodiment of a cement delivery guide 200 may include the same, similar, and/or substantially the same features, components, and functionality as explained above with respect to the first embodiment of a cement delivery guide 100. At least one difference may be that cement delivery guide 200 is configured to facilitate the delivery of cement to a fenestrated bone screw that is coupled to connector, e.g., the extended tulip head connector 70 shown in FIGS. 18-19.

Figure 15:
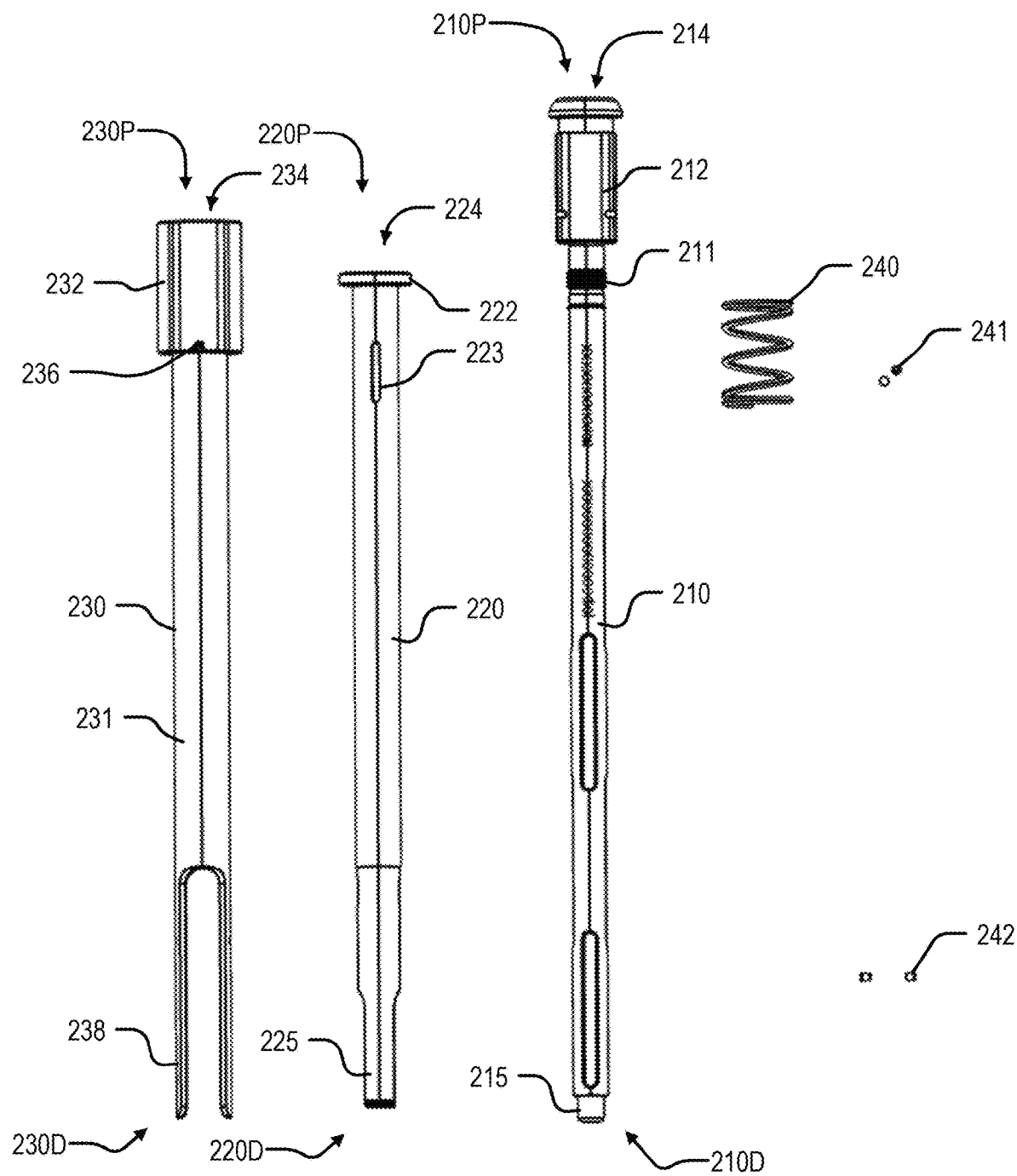
FIG. 15 is a first exploded parts view of a cement delivery guide.
Figure 16:
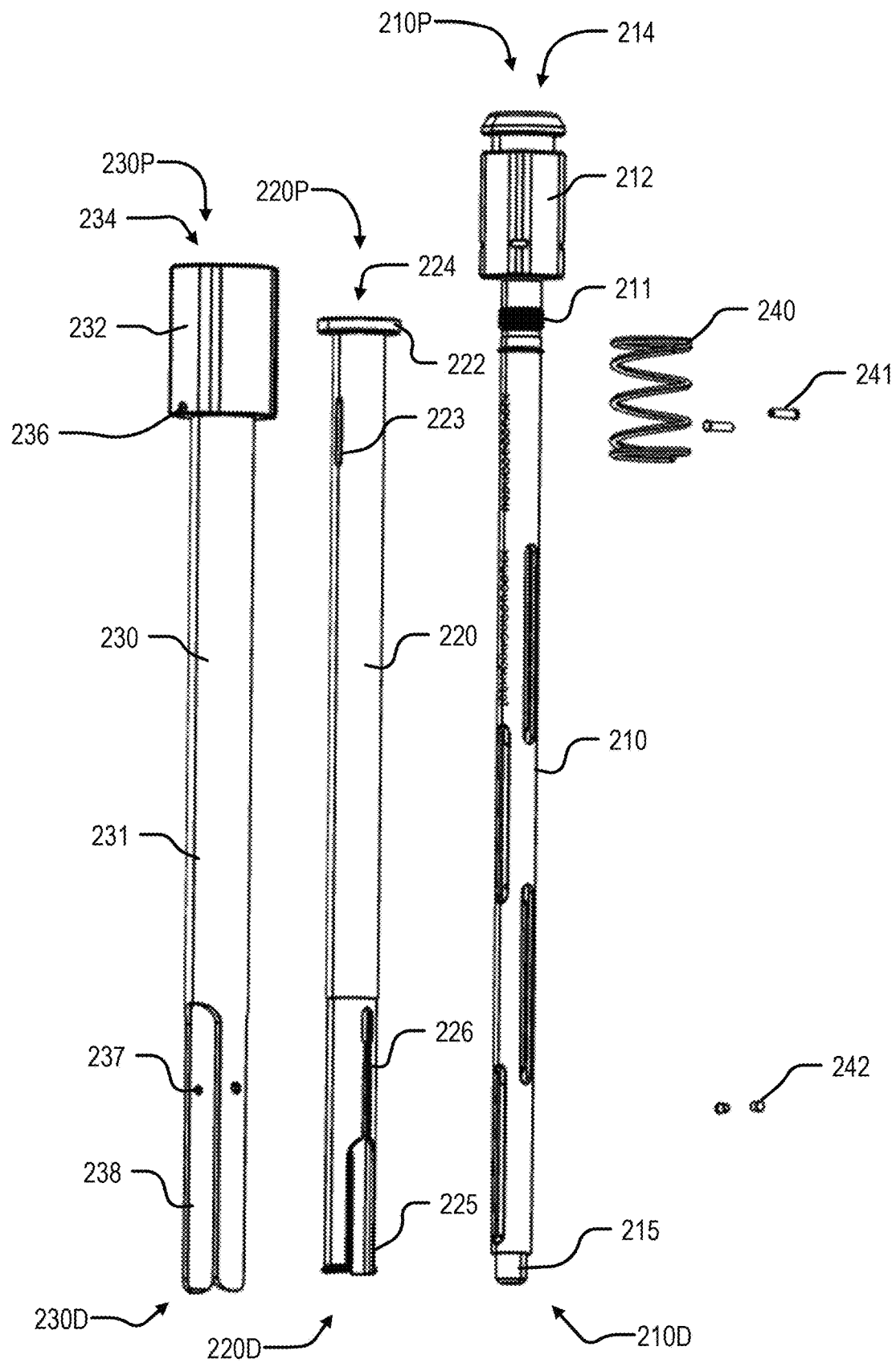
FIG. 16 is a second exploded parts view of a cement delivery guide.
Figure 17:
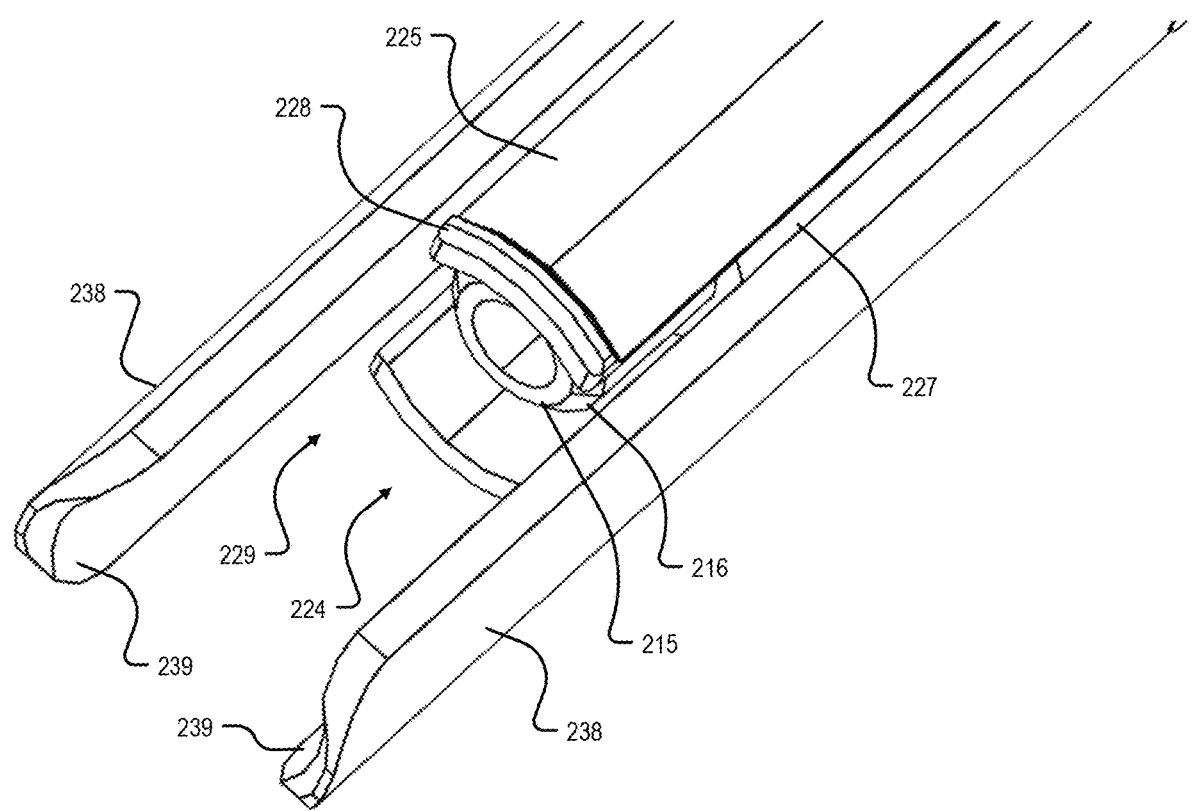
FIG. 17 is an enlarged view of a distal end of a cement delivery guide.
Figure 18:
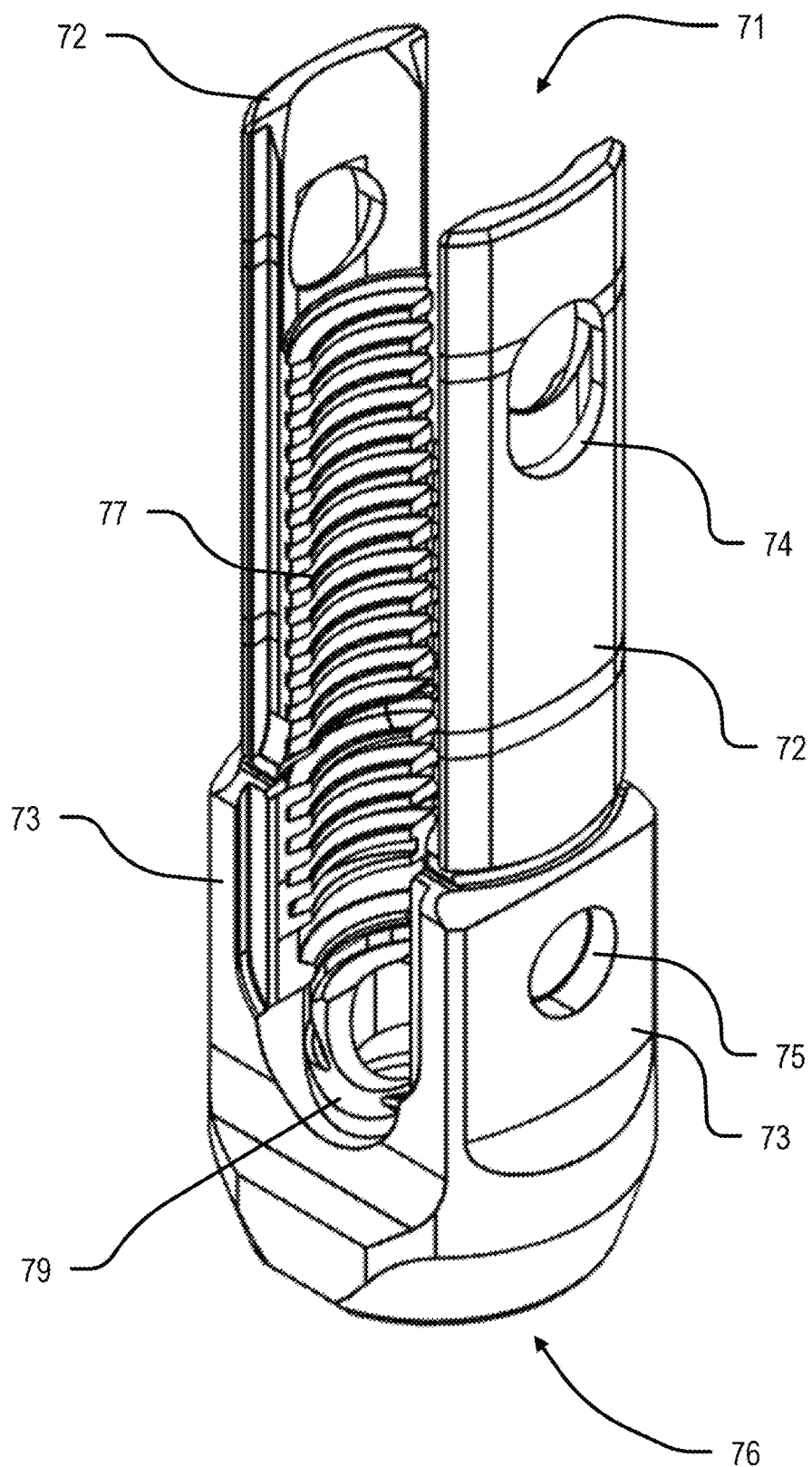
FIG. 18 is perspective view of a connector for use with various cement delivery guides disclosed herein.

FIGS. 12-15 are various perspective views of a cement delivery guide 200. FIGS. 15-16 are various exploded parts views of a cement delivery guide 200. FIG. 17 is an enlarged view of a distal end of a cement delivery guide 200. In the example embodiment, a cement delivery guide 200 extends in a longitudinal direction from a proximal end 200P to a distal end 200D. As seen best in the exploded parts views of FIGS. 15-16, the guide 200 may include a three-part assembly including a hollow outer sleeve 230, a hollow inner sleeve 220, and a hollow inner rod 210. In various embodiments, the outer sleeve 230 extends in a longitudinal direction from a proximal end 230P to a distal end 230D and includes a central aperture 234 extending from the proximal end 230P to the distal end 230D. Additionally, the outer sleeve 230 may include a first portion 232 and a second portion 231 in which the first portion 232 defines a portion of the aperture 234 having a relatively larger interior diameter than the interior diameter of the second portion 231. Furthermore, outer sleeve 230 may include a U-shaped distal end 230D comprising a first engagement tab 238 and a second engagement tab 238. As will be explained in further detail below, engagement tabs 238 may be configured to couple to a spinal connector, e.g., the extended tulip bulb connector 70 of FIG. 18. Although an extended tulip bulb connector 70 is illustrated in FIG. 18, it shall be understood that engagement tabs 238 may be similarly configured to couple to a non-extended tulip bulb connector, e.g., a tulip bulb connector only having a height corresponding to the lower tabs 73 without extended tabs 72 (see FIG. 18). Additionally, in a non-extended tulip bulb connector some persons with skill in the art may refer to tabs 73 as "arms" rather than tabs.

In the example embodiment, the hollow inner sleeve 220 may extend in a longitudinal direction from a proximal end 220P to a distal end 220D and include a central aperture 224 extending from the proximal end 220P to the distal end 220D. In various embodiments, the inner sleeve 220 may be disposed inside of aperture 234 and be movably coupled with the outer sleeve 230 such that the inner sleeve 220 may move forward and backward in the longitudinal direction across a distance generally corresponding to a length of the first portion 232 in the longitudinal direction. In some embodiments, the inner sleeve 220 may move forward and backward in the longitudinal direction across a distance that is less than the full length of the first portion 232 in the longitudinal direction. In the example embodiment, the inner sleeve 220 may include a first positioning slot 223 which may accommodate first positioning pins 241 extending through first pin holes 236 of outer sleeve 230. For example, first positioning pins 241 may extend through first pin holes 236 and into first positioning slot 223 such that inner sleeve 220 may move forward and backward in the longitudinal direction while preventing rotation of inner sleeve 220 relative to outer sleeve 230. In some embodiments, first positioning slot 223 may extend in the longitudinal direction for a specific distance corresponding to the desired length of travel of inner sleeve 220. Additionally, a biasing element such as a coil spring 240 may be disposed inside of the first portion 232 to bias the inner sleeve 220 towards a retracted position. In the example embodiment, a first end of spring 240 may contact the positioning pins 241 and a second end of spring 240 (opposite from first end) may contact stop ring 222. For example, spring 240 may apply a force that urges stop ring 222 of inner sleeve 220 in a proximal direction, i.e., towards proximal end 230P of outer sleeve. In other alternative embodiments, a spring 240 may not be included and/or pins 241, 242 may not be included (not illustrated). For example, the inner sleeve 220 and outer sleeve 230 may be threadably coupled together. As seen best in FIG. 16, engagement tabs 238 may also include a second pin aperture 237 of which second pins 242 may extend therethrough into second positioning slot 226. Similar to the functionality of first positioning slot 223, first positioning pins 241, and first pin holes 236 as explained above, the second positioning slot 226, second positioning pins 242, and second pin holes 237 may facilitate and/or allow inner sleeve 220 to move forward and backward in the longitudinal direction while preventing rotation of inner sleeve 220 relative to outer sleeve 230. In this way, inner sleeve 220 may be movably coupled to outer sleeve 230 such that it may move forward and backward in the longitudinal direction between a neutral position (i.e., the retracted position) and an extended position. As will be explained in more detail below, in the extended position the distal end 220D of the inner sleeve 220 may extend farther than the distal end 230D of outer sleeve 230, e.g., farther in a distal direction. Although the example embodiment illustrates a first and second means for preventing rotation of inner sleeve 220 various other embodiments may only utilize one of the two positioning slots 223, 226, one of the two sets of pin holes 236, 237, and one of the two sets of pins 241, 242.

In the example embodiment, inner rod 210 may extend in a longitudinal direction from a proximal end 210P to a distal end 210D and include a central aperture 214 extending from the proximal end 210P to the distal end 210D. In various embodiments, the inner rod 210 may be removably disposed and/or coupled with inner shaft 220. For example, inner rod 210 may be disposed inside of aperture 224. Additionally, inner rod 210 may include a threaded portion 211 that may thread to a corresponding threaded portion at the proximal end of aperture 224 (see FIG. 12). In this way, the inner rod 210 may be threadably engaged with corresponding threads of aperture 224 having a corresponding size and shape to the thread pattern of threaded portion 211. Accordingly, an end user may couple and uncouple inner rod 210 to inner sleeve 220 by rotating handle 212 thereby engaging the threaded portion 211 of inner rod 210 with the threaded portion of aperture 224. As will be explained in further detail below, the distal end 210D of inner rod may include an engagement feature 215 having a size and shape corresponding to a saddle 79, and a drive feature 52 and/or counterbore 56 opening of a fenestrated bone screw 50 (see FIGS. 8-9) that is accessible through a central aperture of the saddle 79.

As seen best in FIG. 17, engagement tabs 238 may include curved interior side surfaces 239 that are configured to directly contact and couple to curved outer surfaces of engagement tabs 72 of a connector 70 (see also FIG. 18). In various embodiments a size and shape of the engagement tabs 238 and curved interior side surfaces 239 may correspond to a size and shape of extended tabs 72. For example, a spacing between interior side surfaces 239 may correspond to a spacing between a first extended tab 72 and a second extended tab 72 and a radius of curvature of the interior side surfaces 239 may correspond to a radius of curvature that corresponds to a radius of curvature of the outside surfaces of extended tabs 72. Additionally, a distal most tip of the curved interior side surface 239 may be inclined to facilitate an outward splaying motion when the engagement tabs 238 contact the extended tabs 72 such that the inside surfaces of engagement tabs 238 slide along the outside surfaces of extended tabs 72. Additionally, a distal end 220D of inner sleeve 220 may include a coupling portion 229 surrounding a distal end 20D of aperture 224. In the example embodiment, coupling portion 229 may be configured to couple to an interior of a U-shaped passageway of a spinal connector, e.g., the extended tulip bulb connector of FIG. 18. In some embodiments, tangs 225 may be referred to as tabs and/or engagement tabs. In various embodiments, inner sleeve 220 may include at least one deformable tang 225 that is configured to splay inward and/or outward from a central axis of aperture 224, e.g., to splay inward towards a central axis of aperture 224 and to splay outward in a lateral direction opposite the longitudinal extension direction defined by aperture 224. In the example embodiment, coupling portion 229 includes two deformable tangs 225 that are spaced around a portion of the circumference of a distal end 220D of aperture 24. For example, a first tang 225 is opposite a second tang 225 and a gap is formed therebetween first tang 225 and second tang 225 that allows the tangs 225 to splay inward and/or outward when connecting to a spinal connector, e.g., the extended tulip bulb connector of FIG. 18. Each tang 225 may be delineated by slits 227 that form gaps in the distal end 220D and extend in the longitudinal direction from the distal end 220D towards the proximal end 220P for a relatively short distance. In the example embodiment, each slit 227 extends from a distal most end 20D towards slot 226 and each slit 227 is partially defined by the relatively narrower slot 226. For example, slits 227 are relatively wider than and adjoin slots 226. Additionally, an exterior side surface of each tang 225 may include an arcuate rim 228 and/or protrusion. As will be explained in further detail below, this configuration may allow for an elastic deformation in which tangs 225 splay inward momentarily when initially connecting to a spinal connector and then splay outward to seat in a corresponding cavity or rail once positioned deep enough in a U-shaped cavity of the spinal connector (see FIG. 19).

As seen best in FIG. 17, a distal end 210D of inner rod 210 may include an engagement feature 215. In various embodiments, engagement feature 215 may have a size and shape corresponding to a drive feature 52 of a bone screw 50. Accordingly, engagement feature 215 may take any suitable shape corresponding to the particular drive feature 252 of bone screw 50. In various embodiments, engagement feature 215 may have a substantially circular shape as illustrated, or alternatively engagement feature 215 may generally correspond to a torx, polygonal, square, or hexolobular shape, for example. In the example embodiment, engagement feature 215 comprises an annular ring like shape having an inclined portion 216 that generally surrounds a distal most end of aperture 214. In at least one embodiment, an end user may position engagement feature 215 against a positioning saddle 79 such that a distal end of engagement feature 215 extends through a central aperture of positioning saddle 79 and into drive feature 52 of bone screw 50. Additionally, a stop surface 217 may include any suitable geometry for directly contacting the uppermost surface of the positioning saddle 79 of tulip head connector 70 (see FIGS. 18 and 19). For example, stop surface 217 may include various flat surfaces and or curved surfaces having a size and shape generally corresponding to a size and shape of positioning saddle 79.

Figure 19:
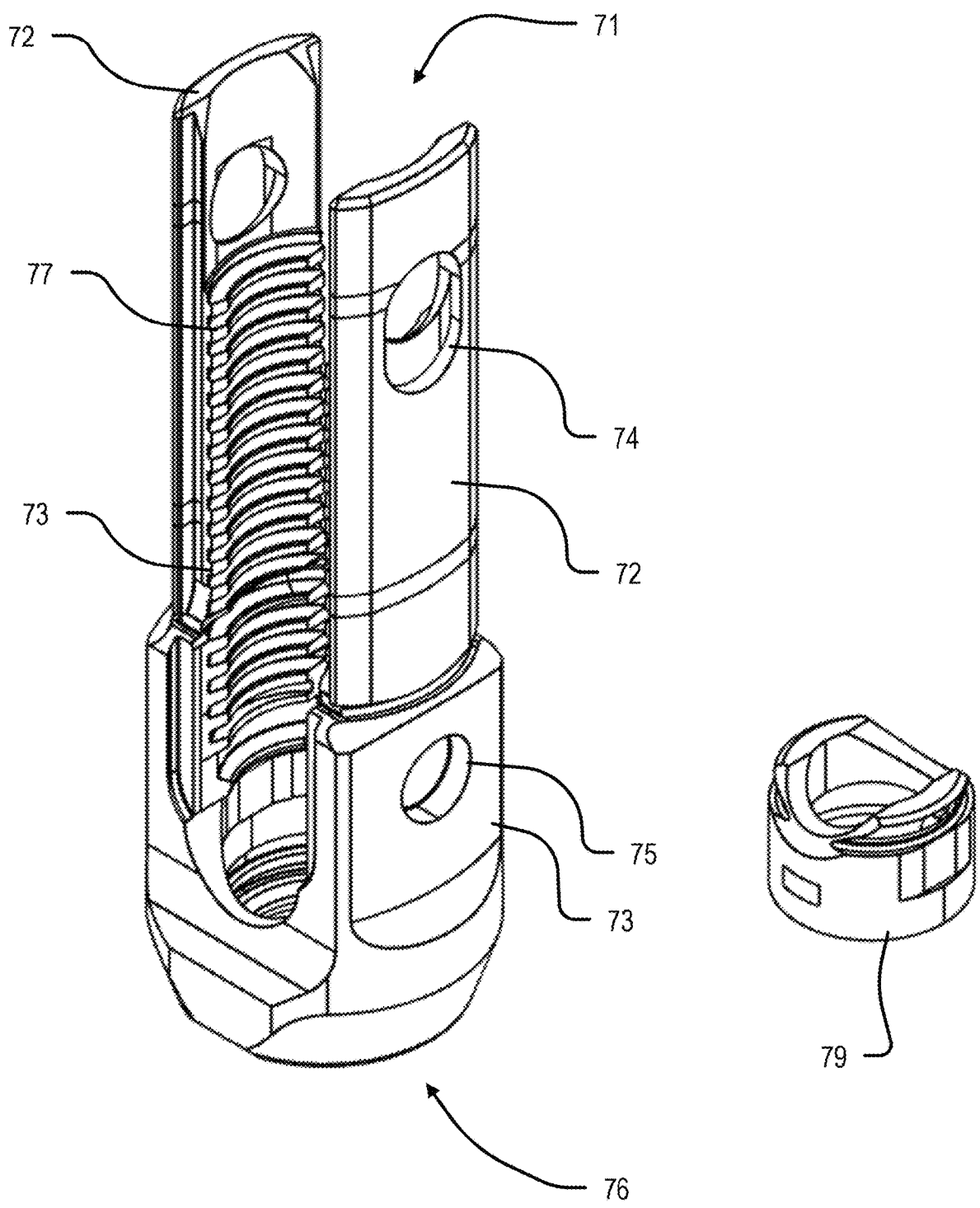
FIG. 19 is a partial exploded parts view of a connector for use with various cement delivery guides disclosed herein.

FIGS. 18-19 illustrate various views of an extended tulip head connector 70. In the example embodiment, extended tulip bulb connector 70 may include a lower cavity 76 for receiving a head portion of a bone screw. In at least one embodiment, the lower cavity 76 is configured to pop on to the head portion of a polyaxial bone screw and may include various nesting rings which allow various washers, clamps, c-shaped rings, etc. (not illustrated) that may secure the head portion 51 of the bone screw 50 to the connector 70. Additionally, connector 70 may include a relatively large U-shaped passageway 71 for receiving a spinal rod (not illustrated). Additionally, the U-shaped passageway 71 may be defined by a first arm and second arm that define a disconnected thread pattern 77 for receiving a set screw (not illustrated) to constrain the spinal rod (not illustrated) when placed therein. In various embodiments, the first arm may comprise a first extended tab 72 and a first lower tab 73 and the second arm may comprise a second extended tab 72 and a second lower tab 73. In at least some embodiments, the extended tabs 72 may be configured as breakoff tabs 74 although this is not a requirement of all embodiments. At least one advantage of breakoff tabs 74 is that they may provide a surgeon with a relatively larger U-shaped passageway 71 to facilitate reducing a spinal rod during a complex reduction procedure. Once the complex reduction procedure is finalized and bone cement has been delivered to the fenestrated bone screw 50, the extended tabs may be broken off. In various embodiments, extended tabs 72 may include first connection apertures 74 and lower tabs 73 may include second connection apertures 75 for coupling a surgical tool, such as a counter torque tool and/or a breakoff tool to the connector 70. In various embodiments, connection apertures 74, 75 may be indentations or they may be through holes. Connector 70 may further include a saddle 79 which has a lower spherical shaped cavity corresponding to a shape of a head portion 51 of a bone screw 50. Additionally, saddle 79 may have a recessed curve portion on an upper surface thereof to accommodate a spinal rod having a cylindrical shape. Furthermore, as explained above, engagement feature 215 may have a size and shape generally corresponding to the geometry of the upper surface of saddle 79.

Figure 20:
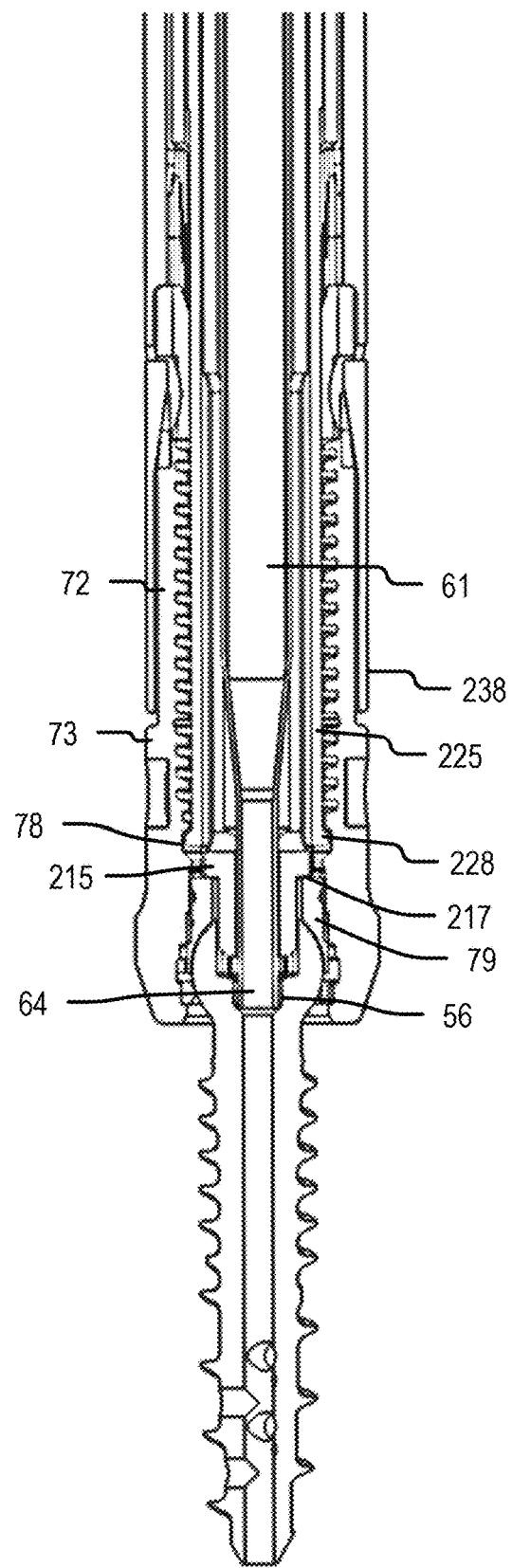
FIG. 20 is a cross section view of a cement delivery guide coupled to a fenestrated bone screw and a cement delivery device inserted into a counterbore of the fenestrated bone screw.

FIG. 20 is a cross section view of bone cement guide 200 and CDD 60 in operation. As illustrated, the extended tulip head connector 70 is securely coupled to bone screw 50. For example, the head portion 51 of the bone screw 50 is securely coupled within the lower cavity 76 of the extended tulip head connector 70. As illustrated, engagement tabs 238 surround and capture the extended tabs 72 of connector 70. For example, the inside surfaces of engagement tabs 238 directly contact the outside surfaces of extended tabs 72. Additionally, tangs 225 extend through the interior of the U-shaped passageway 71 (see FIG. 19) of connector 70 such that the arcuate rim 228 portions of tangs 225 are seated and/or nested within a lower indentation 78. For example, the outside surfaces of tangs 225 and/or arcuate rim 228 portions directly contact the inside surfaces of lower tabs 73 via indentation 78. Additionally, inner rod 210 is threadably engaged with inner sleeve 220 such that engagement feature 215 is partially inserted within drive feature 52 of bone screw 50 while stop surface 217 directly contacts an uppermost surface of saddle 79. Furthermore, CDD 60 may be insert inside of inner rod 210 such that shaft 61 extends therethrough and a tip portion 64 is fully seated inside of counterbore 56. In this way, CDD 60 may deliver bone cement through cement delivery guide 200 directly into the counterbore portion 56 of fenestrated bone screw 50. In the example embodiment, engagement feature 215 may not fully extend into the counterbore portion 56 although in some embodiments it may. For example, in some embodiments, engagement feature 215 (or a portion thereof) may have a length, size, and shape generally corresponding to a size and shape of counterbore 215 such that no CDD is required to deliver bone cement to fenestrated bone screw 50. Additionally, consistent with the scope of this disclosure, in alternate embodiments, engagement feature 215 may have a length, size, and shape generally suitable for the specific type of connector utilized, i.e., the scope of this disclosure is equally suited for both extended and non-extend connectors as disclosed above. Likewise, engagement feature 215 may take alternate shapes depending on the specific geometry of saddle 79, and in various connectors where no saddle 79 is used engagement feature 215 may couple directly to the head of a bone screw similarly as explained above with respect to engagement feature 15 and stop surface 17 of tool 100. Accordingly, it shall be understood that structural aspects, functionality, and design of tool 100 may be interchangeable with tool 200 (and vice versa) unless the context clearly indicates otherwise.

It should be understood that various aspects disclosed herein may be combined in different combinations than the combinations specifically presented in the description and accompanying drawings. For example, features, functionality, and components from one embodiment may be combined with another embodiment and vice versa unless the context clearly indicates otherwise. Similarly, features, functionality, and components may be omitted unless the context clearly indicates otherwise. It should also be understood that, depending on the example, certain acts or events of any of the processes or methods described herein may be performed in a different sequence, may be added, merged, or left out altogether (e.g., all described acts or events may not be necessary to carry out the techniques).

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

What is claimed is:
1. A surgical tool for delivering bone cement, comprising:
   a hollow outer sleeve having an elongated cylindrical shape, a first portion having a first inner diameter and a second portion having a second inner diameter, the first inner diameter being greater than the second inner diameter;
   a hollow inner sleeve having an elongated cylindrical shape, the hollow inner sleeve being disposed inside of the hollow outer sleeve and having a first thread pattern adjacent a proximal end thereof and a coupling portion at a distal end thereof, the hollow inner sleeve being movable between a retracted position and an extended position;

a spring disposed in the first portion biases the hollow inner sleeve towards the retracted position; and a hollow inner rod removably disposable within the hollow inner sleeve and having a distal end configured to guide a flowable material to a bone screw, the hollow inner rod including a second thread pattern having a size and shape corresponding to a size and shape of the first thread pattern;

wherein in the extended position the coupling portion extends beyond a distal end of the hollow outer sleeve and is configured to splay outward to surround and capture a head portion of the bone screw; and wherein in the retracted position the coupling portion is moved inside of the distal end of the hollow outer sleeve and constrained from splaying outward thereby securely coupling the surgical tool to the head portion of the bone screw; and wherein the hollow inner sleeve comprises a stop ring at a proximal end thereof configured to prevent the hollow inner sleeve from moving farther than the extended position.

2. The surgical tool of claim 1, wherein the coupling portion comprises at least one slot extending from the distal end of the hollow inner sleeve and wherein said flowable material comprises bone cement.

3. The surgical tool of claim 1, wherein the coupling portion comprises four slots extending from the distal end of the hollow inner sleeve towards a proximal end of the hollow inner rod.

4. The surgical tool of claim 3, wherein each slot of the four slots is evenly spaced apart from an adjacent slot of the four slots.

5. The surgical tool of claim 1, wherein the coupling portion comprises a lip portion that is configured to retain the bone screw from an underside thereof.

6. The surgical tool of claim 1, further comprising a cement delivery tube that is configured to be disposed within the inner rod.

7. The surgical tool of claim 1, wherein:
the bone screw is a fenestrated bone screw and the head portion comprises a counter bore, and
the hollow inner rod is configured to delivery bone cement along an axis that is coaxial with the counter bore.

8. The surgical tool of claim 7, further comprising a cement delivery tube that is configured to be disposed within the inner rod,
wherein the cement delivery tube includes a distal end having a size and shape corresponding to a size and shape of the counter bore.

9. The surgical tool of claim 1, wherein:
the bone screw is a fenestrated bone screw and the head portion comprises a counterbore; and
the distal end of the hollow inner rod comprises an engagement feature configured to contact the head portion of the fenestrated bone screw, the engagement feature including a distal end including a central opening therein having a size and shape corresponding to a size and shape of the counterbore.

10. A surgical system for delivering bone cement to a target site, comprising:
a medical implant including a U-shaped connector having a first connection tab and a second connection tab opposite the first connection tab, the U-shaped connector being configured to couple to a head portion of a bone screw in a lower cavity;

a hollow outer sleeve having an elongated cylindrical shape and a distal end comprising a first engagement tab and a second engagement tab opposite the first engagement tab, the first engagement tab being configured to couple to the first connection tab and the second engagement tab being configured to couple to the second connection tab;

a hollow inner sleeve having an elongated cylindrical shape and a distal end comprising a third engagement tab and a fourth engagement tab opposite the third engagement tab, the hollow inner sleeve being disposed inside of the hollow outer sleeve and having a first thread pattern at a proximal end thereof, the hollow inner sleeve being movable between a retracted position and an extended position; and a hollow inner rod removably disposable within the hollow inner sleeve and having a distal end configured to guide bone cement to the head portion of the bone screw while it is disposed in the lower cavity of the U-shaped connector, the hollow inner rod including a second thread pattern having a size and shape corresponding to a size and shape of the first thread pattern, wherein in the extended position the third engagement tab and the fourth engagement tab each extend beyond the distal end of the hollow outer sleeve, and wherein in the retracted position the first engagement tab and the second engagement tab extend beyond the distal end of the hollow inner sleeve.

11. The system of claim 10, wherein an inside surface of the first engagement tab is configured to directly contact an outside surface of the first connection tab and an inside surface of the second engagement tab is configured to directly contact an outside surface of the second connection tab.

12. The system of claim 11, wherein the inside surface of the first engagement tab comprises an inclined end and the inside surface of the second engagement tab comprises an inclined end.

13. The system of claim 11, wherein the third engagement tab comprises an arcuate rail on an outside surface thereof and the fourth engagement tab comprises an arcuate rail on an outside surface thereof.

14. The system of claim 13, wherein in the extended position, the arcuate rail of the third engagement tab is configured to nest within a first channel of the U-shaped connector and the arcuate rail of the fourth engagement tab is configured to nest within a second channel of the U-shaped connector.

15. The system of claim 10, wherein in the extended position the third engagement tab and the fourth engagement tab each directly contact opposite interior sidewall surfaces of the U-shaped connector.

16. The system of claim 10, further comprising a cement delivery tube that is configured to be disposed within the inner rod.

17. The system of claim 16, wherein the bone screw is a fenestrated bone screw and the head portion comprises a counter bore.

18. The surgical tool of claim 17, wherein the cement delivery tube includes a distal end having a size and shape corresponding to a size and shape of the counter bore.

19. The surgical tool of claim 10, wherein:
the bone screw is a fenestrated bone screw, and the head portion comprises a counterbore; and
the distal end of the hollow inner rod comprises an engagement feature configured to contact the head portion of the fenestrated bone screw, the engagement feature including a tip portion defining a central opening having a size and shape corresponding to a size and shape of the counterbore.

\* \* \* \* \*